United States Patent [19]
Cutts, Sr.

[11] Patent Number: 5,617,616
[45] Date of Patent: Apr. 8, 1997

[54] OSTOMY POUCH CLOSURE CLAMP

[76] Inventor: Edmund A. Cutts, Sr., P.O. Box 9, Oxford, Md. 21654

[21] Appl. No.: 478,694
[22] Filed: Jun. 7, 1995
[51] Int. Cl.⁶ ................................................. B65D 77/10
[52] U.S. Cl. ........................... 24/30.5 R; 74/487; 74/517; 74/544
[58] Field of Search ............................ 24/30.5 R, 30.5 P, 24/460, 462, 459, 518, 517, 487, 544; 604/332, 335

[56] References Cited

U.S. PATENT DOCUMENTS

| | | | |
|---|---|---|---|
| 1,059,051 | 4/1913 | Lapp | 24/517 |
| 2,496,175 | 1/1950 | Perry | 604/332 |
| 3,523,534 | 8/1970 | Nolan | 604/332 |
| 4,551,888 | 11/1985 | Beecher | 24/30.5 P |
| 4,648,160 | 3/1987 | Spinosa et al. | 24/30.5 R |
| 4,834,730 | 5/1989 | Holtermann et al. | 604/335 |
| 4,983,172 | 1/1991 | Steer et al. | 604/332 |
| 4,991,267 | 2/1991 | Apperson et al. | 24/30.5 R |
| 5,125,133 | 6/1992 | Morrison | 24/30.5 R |
| 5,375,300 | 12/1994 | Chen | 24/30.5 R |

FOREIGN PATENT DOCUMENTS 574954  7/1924  France ..................... 24/461

Primary Examiner—James R. Brittain
Attorney, Agent, or Firm—Dalton L. Truluck

[57] ABSTRACT

An ostomy pouch clamp for closing off the bottom end of the pouch having pivoted clamping elements, one element having a trough channel for receiving the other blade element therein. The improvement in this clamp results from (1) single or multiple knife like sealing ribs or lip edges on the blade member bottom for engaging the pouch walls against a flat bottom of the trough channel and (2) latch means located midway between the ends of the clamping elements for pressing the two elements together (as well as releasing them) and producing an audible snapping signal to alert the user that the latch means is in the proper location. The latch means is easy to locate by the user and distributes the force pressing the elements together more equally than prior art devices.

19 Claims, 1 Drawing Sheet

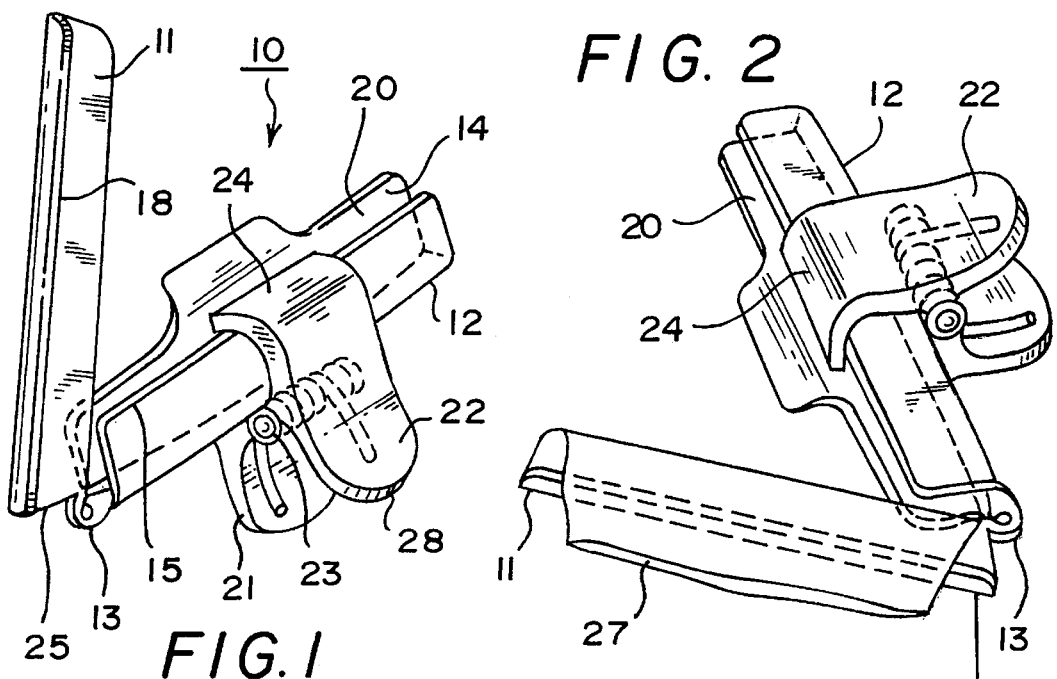
FIG. 1
FIG. 2
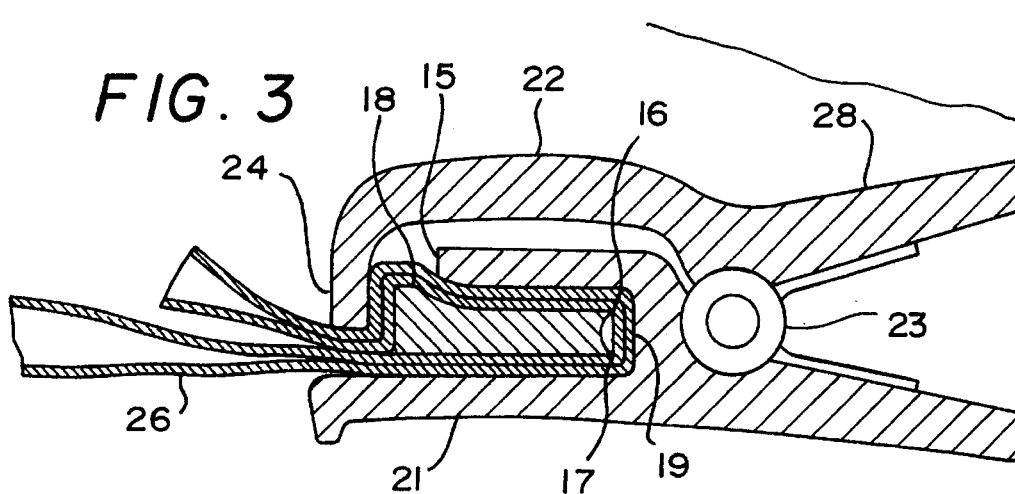
FIG. 3
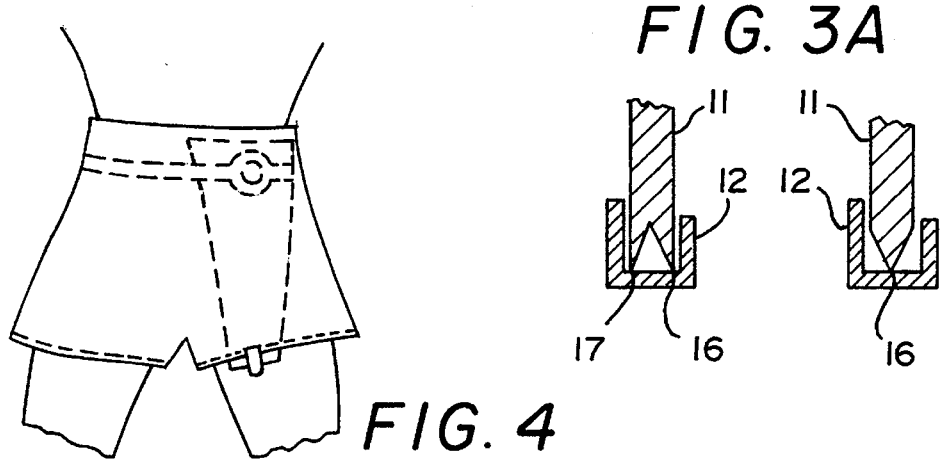
FIG. 3A
FIG. 4

OSTOMY POUCH CLOSURE CLAMP

FIELD OF THE INVENTION

This invention relates to a device for receiving body waste discharge from a surgically formed opening (stoma) in a patient's abdomen e.g., colostomy or iliostomy. Conventionally, a plastic or elastomeric bag or pouch is positioned over the surgically formed stoma to receive the body waste through an inlet opening in the bag's upper portion. The bag also has a drainage opening located at the bottom of the bag. Typically in the past, the body waste was retained in the bag by means of a closure element e.g., pressure clamp, sealing off the bag's bottom opening. The bag could then be emptied by merely releasing the closure means over an appropriate toilet receptacle to permit drainage of the waste contents thereinto. The invention herein described is directed to an improvement in closure means for sealing off the open bottom end of the drainage bag and for ease in opening the closure means to permit drainage. Another improvement produced by this invention is that of an audible signal to alert the patient that the sealing of the bag is completed.

DESCRIPTION OF PRIOR ART

Prior art patent examples relating to the invention are U.S. Pat. No. 2,496,175 (Perry), U.S. Pat. No. 3,523,534 (Nolan), U.S. Pat. No. 4,834,730 (Holtermann et al), U.S. Pat. No. 4,983,172 (Steer et al) and U.S. Pat. No. 5,125,133 (Morrison). The prior art devices generally show bag pinch type clamps which seal off the bag bottoms. These prior art bag closures often do not seal the bag completely which can easily result in unsanitary conditions for the user. Also some prior art types are hard to release from the bag due to the type latching means provided on the closure member. A good example of the typical closure means used as the standard in the medical field today is the bag clamp shown in Nolan U.S. Pat. No. 3,523,534 cited supra. Note that this conventional clamp device does not have a single or multiple line seal and is latched at one end of the clamp which is generally difficult to release. This type clamp also could break off at the latch means during use resulting in a disastrous situation for the patient. The remaining patents all are similar to the Nolan device described and have many of the same disadvantages.

SUMMARY OF THE INVENTION

The essential improved concept of the invention is twofold. First the device has a clamp blade member that has single or multiple bag engaging V-shaped ribs or lip edges for sealing against a flat bottom of an anvil trough member to provide a line seal on the bag clamped therebetween. Second, the device has a spring biased latching means interposed between the ends of the respective blade and anvil members for maintaining the members in sealing engagement around the bag. The spring biased latch means also snaps into place over a stepped rib portion on the blade member of the closure device thereby producing an audible click or snap so that the patient is instantly aware that the device is properly situated.

The device is easy to manufacture and clean by virtue of its simple design. Also the overall size of the device is reduced facilitating operation by feeble patients.

BRIEF DESCRIPTION OF THE DRAWINGS

FIG. 1 is a perspective view of the pouch clamp of this invention, the clamp being shown in open condition.

FIG. 2 is a similar view of the pouch clamp with the pouch folded over the blade member prior to closing the clamp.

FIG. 3 is a cross sectional view of the clamp closed over the bag with the spring biased latch means engaged.

FIG. 3A is a simplistic alternative cross-sectional view of the clamping elements engaged showing both single and plural sealing lip edges.

FIG. 4 is a partial view of the abdomen of a patient's torso with a surgical pouch in use including the closure device of the invention.

DETAILED DESCRIPTION OF THE INVENTION

Referring to the drawings, numeral 10 designates a clamp of the general type disclosed in the aforementioned U.S. Pat. No. 3,523,534. The clamp of the invention includes a first clamping blade member 11 pivotally connected to a second blade receiving trough member 12 by means of a hinge element 13. The first blade member 11 has a bottom clamp surface having at least one V-shaped rib or lip edge 16, 17 extending longitudinally of the blade member. It is to be noted that whereas two V-shaped lip edges are shown in FIG. 3, multiple or even a single sealing V-shaped lip may be employed without departing from the scope of the invention in which see FIG. 3A. In addition the blade member 11 has a step portion 18 extending laterally from the top portion along the length thereof.

The second blade receiving trough member 12 has an open ended channel 20 formed by side walls 14, 15 extending upwardly from a flat bottom interior surface 19. The interior width of the trough flat bottom is approximately the same width as the blade member bottom clamp surface. Note that side wall 15 is shorter than side wall 14 in order to accommodate step portion 18 when blade member 11 is fully received in channel 10 (FIG. 3). The trough member also includes a base portion 21 extending outwardly away from the trough in a general continuation of side wall 15. This base portion can be a separate piece attached to the trough member or made integral therewith.

The hinge 13 is constructed integrally with the bottom of trough member 12 and extends outwardly (as in FIG. 1) to connect with the end 15 of blade member 11. The various parts of the device can be made of a durable plastic such as nylon or polypropylene.

The means for latching the two above described clamping members together is located between the ends of the hinged members 11, 12. Reference is made to FIGS. 1 and 3 wherein a pivoted clamping element 22 with finger actuating lever 28 is attached to base portion 21 by means of a spring 23. The spring can be a coil as shown, a convoluted wire or other equivalent type of spring. Note that the front portion 24 of element 22 is curved so as to fit around and over the front end of side wall 15 to simultaneously force blade member 11 into channel 20 (by engagement with stepped portion 18) and latch them together. Also this latching element produces an audible snapping or latching sound alerting the patient that the device is in place.

In use, the device operates in the following manner. An ostomy bag 26 with open bottom 27 is folded over the blade member 11 (as shown in FIG. 2) while members 11 and 12 are pivoted apart. The two members are then clamped together with the bag inbetween (FIG. 3). Meanwhile, the spring clamping element 22 is then actuated by squeezing lever 28 to open element 22 and then releasing same to close over the front end of the trough side wall 15. The closing of spring clamping element forces blade 11 into contact with trough flat bottom 19. The V-shaped lip or lip edges 16, 17 of blade 11 thereby engage the bag against the flat bottom 19 to form a knife-edged lip seal across the folded bag on each side of the trough bottom. As indicated earlier, multiple or single V-shaped lip edges may be used to form the knife-edge seal. This type of seal is a direct positive seal and eliminates any need for a "side wedging" seal shown by some of the prior art devices. In addition to the above description of the spring clamping element forcing the blade 11 into the channel 20, it should be pointed out that the stepped portion 18 is the portion actually engaged by front portion 24 to force the blade member into channel 20 in the trough member. The feature of wall 15 being shorter than sidewall 14 provides a recess which accommodates the stepped portion 18 which is then engaged by the spring clamp element front portion 24. Thus with the bag bottom sealed, the ostomy bag is mounted on the patient in the conventional manner. After receiving body waste the bag may be emptied by easily unlatching the spring clamped element 22 manually from engagement around the blade and trough members. No hunting or feeling around for an end latching means is necessary. The spring clamp is released by squeezing the lever 28 and base 21 together by the thumb and forefingers. In addition, the base member engaging against the abdomen renders the device relatively non-traumatizing. Also the base 21 when worn if pressed against an external object, such as a table, will sink into the fleshy tissue, keeping the spring lever 28 from applying the required force to open the spring clamp thus providing an additional safety factor for the patient. After use the device is easily cleaned and reinstalled on a bag for reuse.

Another feature of the invention is shown in FIG. 4 wherein the clamp 10 is depicted as being clamped to the patient's underclothing thereby keeping the clamp device away from the crotch area. Finally, the positioning of the latch means intermediate the ends of the clamping elements instead of at the ends results in shorter length clamp thus providing more comfort for the wearer.

As can be seen from the above description, the present invention has many advantages over the prior art devices in that it is easily accessible by the patient, easily cleaned by virtue of the unobstructed channel and has knife edge sealing. The latch means is greatly improved over prior art latches and produces an audible latching sound when placed into position. Another advantage is that more equal pressure distribution on bag sealing results therefrom due to the central location of the latch means. Another advantage can be gained by merely positioning the axis of the spring clip hinge outwardly which produces a more downward pressure against the bag at the top of the closure.

While in the foregoing, I have disclosed an embodiment of the invention in considerable detail for purposes of illustration, it will be understood by those skilled in that art that any of these details may be varied without departing from the spirit and scope of the invention.

I claim:

1. A clamp device for closing the lower open end of an ostomy pouch, said device including first and second clamping elements pivotally connected together by hinge means at a common end thereof to engage and seal off the pouch lower end and also including latch means to secure the clamping elements in engagement on the pouch:

said first clamping element being an elongated blade member with top and bottom edges, said top edge extending along the length of said blade member, said bottom edge surface having a V shape formed by a longitudinally extending lip portion, said second clamping element being a U shaped trough member with an interior flat bottom forming an open top channel which can receive the blade member therein for clamping off the pouch;

said blade and trough members when clamped about the pouch walls producing a knife edge seal by virtue of the V-shaped lip portion on the blade member pressing the pouch walls against said flat interior bottom of the trough member; said latch means connected to one of either the trough or blade members to maintain said members in place around said pouch and wherein said latch means is connected to the clamping elements at a point between the ends of said elements.

2. A clamp device as in claim 1 wherein said blade member top edge is provided with a laterally extending stepped portion along the length of the blade member.

3. The clamp device as in claim 2 wherein said trough member has dual side walls, one wall being shorter than the other whereby the stepped portion of said blade member is received thereagainst when the said blade and trough members are brought together.

4. A clamp device as in claim 3 wherein said latch means includes a spring clamp pivotally connected to one external side of said trough member, said spring clamp having a front edge surface that engages the stepped portion of said blade member to force the blade member into engagement with the trough member, said stepped portion being pressed into contact with the pouch at said short wall of the trough.

5. A clamp device as in claim 4 wherein the external trough side opposite the spring clamp is relatively flat so as to facilitate the clamp lying flat against the patient when the spring clamp is being actuated.

6. A clamp device as in claim 4 wherein the spring clamp is provided with a spring means that normally biases the spring clamp closed so that when the spring clamp is actuated, the force of the spring means snapping back into closed position acts an audible signal to the user that the ostomy clamp is secure.

7. A clamp device as in claim 2 wherein said latch means is attached only to the trough member.

8. A clamp device as in claim 1, wherein said channel in said trough member is unobstructed throughout its length so as to permit easy wipe cleaning of the channel.

9. A clamp device as in claim 1 wherein said hinge means comprises a flexible unitary piece extending from one end of the trough bottom and joined to said blade bottom edge at common ends thereof.

10. A clamp device as in claim 1 wherein the latch means includes a spring clamp pivotally connected to said clamping elements, said spring clamp having a handle portion and a front clamping edge for engaging over the wall of the trough to press said blade member down into the trough member thereby clamping off the pouch.

11. A clamp device as in claim 1 wherein the clamping elements are made of durable rigid plastic.

12. A clamp device for closing the lower open end of an ostomy pouch, said device including first and second clamping elements pivotally connected together by hinge means at a common end thereof to engage and seal off the pouch lower end and also including latch means to secure the clamping elements in engagement on the pouch:

said first clamping element being an elongated blade member with top and bottom edges, said top edge extending along the length of said blade member, said bottom edge surface having a V shape formed by a longitudinally extending lip portion, said second clamping element being a U shaped trough member with an interior flat bottom forming an open top channel which can receive the blade member therein for clamping off the pouch;

said blade and trough members when clamped about the pouch walls producing a knife edge seal by virtue of the V-shaped lip portion on the blade member pressing the pouch walls against said flat interior bottom of the trough member;.

said latch means connected to one of either the trough or blade members to maintain said members in place around said pouch;

wherein the bottom edge of said blade member is provided with parallel spaced apart V-shaped lip portions to provide multiple knife edge seals on the pouch walls gripped therebetween.

13. A clamp device for an ostomy pouch comprising two pivotally connected clamping elements for sandwiching the pouch therebetween, said clamping elements being pivoted together at one of their ends and having means thereon for forming a closure seal on the pouch when the two elements are clamped together and latching means for securing the two clamping elements together, said latching means being a spring clamp located intermediate the ends of said clamping elements.

14. A clamp device as in claim 13 wherein said spring clamp has a front edge surface that curves down over and around said clamping element to aid in forcing said elements together over said pouch and in maintaining the elements together.

15. A clamp device as in claim 14 wherein said spring clamp is pivotally connected to said clamp device on one external side thereof by a spring means which normally biases the spring clamp to a closed position whereby when the spring clamp is actuated, an audible snapping sound is generated alerting the user that the pouch is securely clamped off.

16. A clamp device as in claim 15 wherein the external side of the clamp device opposite said spring clamp location is generally flat so that engagement thereof with the patient's abdomen is non-traumatizing.

17. A clamp device as in claim 13 wherein said spring clamp includes means for producing an audible signal to the patient that the clamp device is securely fastened onto the pouch.

18. An ostomy bag clamp comprising first and second clamping elements pivotally connected together to seal off an ostomy bag when clamped thereover, said clamping elements each having a first end, a second end and one of said corresponding first or said corresponding second ends being pivotally connected together and a bag clamping engaging surface therebetween and latch means for retaining said clamping elements in place around the ostomy bag, said latch means being located on one of said clamping elements between said ends thereof to provide a more equal distribution of pressure on the clamped elements when engaged thereover.

19. An ostomy bag clamp as in claim 18 wherein said latch means is located centrally of said clamping element ends.

* * * * *